United States Patent [19]

de Koning et al.

[11] Patent Number: 4,582,883
[45] Date of Patent: Apr. 15, 1986

[54] COMPOSITIONS CONTAINING MALEIMIDE-AMIDE COMPOUNDS AS WELL AS THE PREPARATION AND APPLICATION THEREOF

[75] Inventors: Adrianus J. de Koning, Munstergeleen; Jacobus A. Loontjens, Meerssen; Hubertus A. M. Mostert, Geleen; Hubertus A. A. Omloo, Landgraaf, all of Netherlands

[73] Assignee: DSM Resins B.V., Zwolle, Netherlands

[21] Appl. No.: 650,080

[22] Filed: Sep. 13, 1984

[30] Foreign Application Priority Data

Sep. 20, 1983 [NL] Netherlands ............... 8303229

[51] Int. Cl.$^4$ .................................. C08F 226/06
[52] U.S. Cl. ....................................... 526/262
[58] Field of Search ........................... 526/262

[56] References Cited

U.S. PATENT DOCUMENTS

| | | | |
|---|---|---|---|
| 3,018,290 | 1/1962 | Sauers et al. | 260/326.3 |
| 3,763,087 | 10/1973 | Holub et al. | 260/41 R |
| 4,107,174 | 8/1978 | Baumann et al. | 526/263 |
| 4,269,961 | 5/1981 | Jones et al. | 526/262 |
| 4,277,582 | 7/1981 | Mueller et al. | 525/421 |
| 4,289,720 | 11/1981 | Yamazaki et al. | 526/262 |
| 4,323,662 | 4/1982 | Oba et al. | 526/262 |
| 4,374,235 | 2/1983 | Culbertson et al. | 526/262 |

FOREIGN PATENT DOCUMENTS

| | | |
|---|---|---|
| 0051687 | 5/1982 | European Pat. Off. . |
| 1137592 | 12/1968 | United Kingdom . |
| 2010866 | 7/1979 | United Kingdom . |

OTHER PUBLICATIONS

Kumar, "An Efficient in situ Preparation of bis-maleimides Derived from Aromatic Diamines" *Chem. and Ind.*, pp. 189–191 (Mar. 21, 1981).

*Primary Examiner*—Harry Wong, Jr.
*Attorney, Agent, or Firm*—Cushman, Darby & Cushman

[57] ABSTRACT

The invention relates to compositions containing 80–30 weight % of bismaleimide-compounds, 5–60 weight % maleimide-amide compounds and 1–10 weight % maleic anhydride derivative. The invention further relates to the preparation of such compositions and to homogeneous curable compositions comprising bismaleimide-/-maleimide-amide/maleic anhydride compositions according to the invention. The obtained copolymers show good chemical resistance and a high heat distortion temperature.

7 Claims, No Drawings

COMPOSITIONS CONTAINING MALEIMIDE-AMIDE COMPOUNDS AS WELL AS THE PREPARATION AND APPLICATION THEREOF

FIELD OF THE INVENTION

The invention relates to compositions of compounds containing on the one hand a maleimide group and on the other hand an amide group, in combination with bismaleimide compounds, and processes for the preparation of such compositions.

The invention further relates to thermosetting compositions and polymers and objects obtained by curing of these, in which a combination of bismaleimide and maleimide-amide compounds is used.

BACKGROUND OF THE INVENTION

It is known to apply bismaleimides as bifunctional monomer or comonomer in compositions that are cured thermally, through an additional reaction or via radicals. The disadvantage of bismaleimides is that they are soluble in few other copolymerizable compounds. Thus, it has been found to be impossible to dissolve more 10 wt.-% of a bismaleimide in styrene. This is a disadvantage, because styrene is a monomer that can easily be polymerized, is inexpensive and, moreover, has a good chemical resistance. The object of the invention is the preparation of compositions and copolymers in which both styrene or an other copolymerizable compound and a substantial amount of a bismaleimide are used.

SUMMARY OF THE INVENTION

The invention relates to compositions containing 80–30 weight percent of bismaleimide-compounds, 5–60 weight percent maleimide-amide compounds and 1–10 weight percent maleic anhydride derivative. The invention further relates to the preparation of such compositions and also to curable compositions comprising bismaleimide/maleimide-amide/maleic anhydride compositions as described herein. The obtained copolymers show good chemical resistance and a high heat distortion temperature.

The present invention provides compositions with bismaleimides that readily dissolve in ethylenically unsaturated compounds.

The compositions according to the invention comprise:

(a) 80 to 30 wt. % (of a mixture) of compound(s) having the general formula

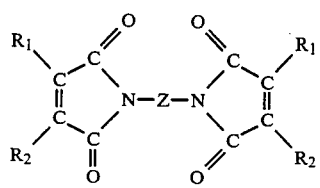

and/or

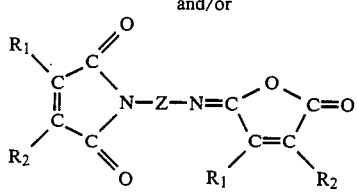

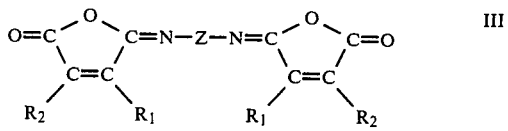

where $R_1$ and $R_2$ each and independently represent a hydrogen atom, an aliphatic, cycloaliphatic or aromatic group containing 1–12 carbon atoms, or a halogen atom, or where $R_1$ and $R_2$, together with the carbon atoms to which they are bound, form a ring system with at least one polymerizable c=c bond, while Z represents a bivalent organic group.

(b) 5 to 60 wt. % of (a mixture of) compound(s) having the general formula

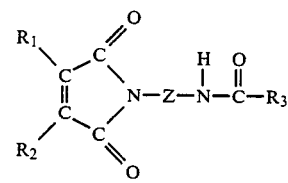

and/or

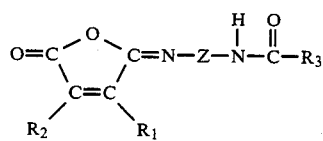

where $R_1$ and $R_2$ each and independently represent a hydrogen atom, an aliphatic, cycloaliphatic or aromatic group containing 1–12 carbon atoms, or a halogen atom, or where $R_1$ and $R_2$, together with the carbon atoms to which they are bound, form a ring system with at least one polymerizable c=c bond, while Z represents a bivalent organic group and $R_3$ an optionally substituted alkyl, cycloalkyl, aralkyl or alkylaryl group, with 1–12 carbon atoms in the alkyl part.

(c) 1 to 10 wt. % of a maleic anhydride derivative having the formula

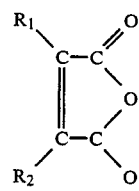

where $R_1$ and $R_2$ each and independently represent a hydrogen atom, an aliphatic, cycloaliphatic or aromatic group containing 1–12 carbon atoms, or a halogen atom, or where $R_1$ and $R_2$, together with the carbon atoms to which they are bound, form a ring system with at least one polymerizable c=c bond.

The compounds according to formula I (bismaleimides), formula II (maleimide-isomaleimides) and formula III (bisisomaleimides) are isomeric compounds, for which the common term 'bismaleimide compounds' will be used in this specification, in the same way as the common term 'maleimide-amide compounds' will be used for the compounds according to formula IV (maleimides-amides) and formula V (isomaleimide-amides) as isomeric compounds.

Maleimide-amide compounds are known per se from Chemistry and Industry 6, 1981, pp. 189-191, as a minor impurity of bismaleimides.

The compounds according to the invention that contain at least 5 wt. % 'maleimide-amide compounds(s)' can be prepared in a very convenient manner by a method that also is the object of the invention and that is characterized in that a diamine having the formula

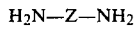    VII where Z has the meanings indicated, is reacted with a maleic anhydride derivative having formula VI in a molar ratio of diamine to maleic anhydride derivative of 1:0.75 to 1:2.5 and in that the mixture obtained is subsequently reacted, in the presence of a suitable catalyst, with an adapted amount of anhydride of an alkylcarboxylic acid with 2 to 7 carbon atoms, this being effected in such a way that in the mixture ultimately obtained the desired ratio between (iso)maleimide groups formed by cyclodehydration, the amount of alkylamide groups formed by (re-)alkylamidation and the amount of acid anhydride compound is obtained.

For the preparation of homogeneous, curable compositions with ethylenically unsaturated compounds it is not necessary to separate the components from the mixture obtained, removal of any solvent used, the alkylcarboxylic acid formed and any excess of alkylcarboxylic anhydride being sufficient.

In the mixtures thus obtained, mostly about 30-50% of the maleimide groups will be present in the isomeric isomaleimide form. The mixture thus will mainly contain bismaleimide, maleimide-isomaleimide and bisisomaleimide compounds, maleimide-amide and isomaleimide-amide compounds and maleic anhydride derivatives. Moreover, depending on the reaction conditions, small amounts (up to about 5%) of amide-amide compounds may be present and possibly, to an even more limited extent, compounds with amide acid groups.

Said compositions according to the invention, that comprise 'bismaleimide compounds', 'maleimide-amide compounds' and acid compounds, appear to be soluble as such in simple solvents such as acetone or methylethylketone, but also in ethylenically unsaturated compounds.

Solutions of the compositions according to the invention in a non-reacting solvent, either in the presence or in the absence of further comonomer(s), for instance diamines, are very suitable for applications such as prepregs, etc. Solutions in copolymerizable compounds with an ethylenically unsaturated c=c bond, lead to homogeneous, curable compositions, that are also the object of the invention and that consist of:

(a) a compound with an ethylenically unsaturated c=c bond, (b) a composition according to the invention which comprises 'bismaleimide compounds', 'maleimide-amide compounds' and an acid anhydride compound, in such an amount that the weight ratio between ethylenically unsaturated compound and composition according to the invention is 2:1 and 1:4, (c) if desired, one or more customary additives, such as inhibitors, curing catalysts, fillers, reinforcing agents and pigments.

Such homogeneous, curable compositions can, in conformity with the invention, be cured, with the aid of a radicals donating initiator, yielding copolymer objects, in particular objects of copolymers consisting of units derived from:

(a) an ethylenically unsaturated compound, (b) compounds having formulae I, II and/or III, where $R_1$ and $R_2$ each and independently represent a hydrogen atom, an aliphatic, cycloaliphatic or aromatic group containing 1-12 carbon atoms, or a halogen atom, or where $R_1$ and $R_2$, together with the carbon atoms to which they are bound, form a ring system with at least one polymerizable c=c bond, while Z represents a bivalent, organic group, (c) compounds having formula IV and/or V, where $R_1$ and $R_2$ each and independently represent a hydrogen atom, an aliphatic, cycloaliphatic or aromatic group containing 1-12 carbon atoms, or a halogen atom, or where $R_1$ and $R_2$, together with the carbon atoms to which they are bound, form a ring system with at least one copolymerizable c=c bond, Z represents a bivalent, organic group and $R_3$ an optionally substituted alkyl, cycloalkyl, aryl, aralkyl or alkylaryl group with 1-12 carbon atoms in the alkyl part, (d) a maleic anhydride derivative having formula VI where $R_1$ and $R_2$ each and independently represent a hydrogen atom, an aliphatic, cycloaliphatic or aromatic group containing 1-12 carbon atoms, or a halogen atom, or where $R_1$ and $R_2$, together with the carbon atoms to which they are bound, form a ring system with at least one polymerizable c=c bond, (e) if desired, one or more other (co)polymerizable monomer or polymer compounds, the weight ratio of a:(b+c+d) being between 2:1 and 1:4, b being from 80 to 30 wt.-%, c from 5 to 60 wt.-% and d from 1 to 10 wt.-% of the amount of b+c+d.

From EP-A-No. 83201582.0 homogeneous, curable compositions are known which comprise bismaleimide compounds, vinyl aromatic compounds and effective amounts of solubility-promoting acid compounds.

According to the invention, as stated, use is made of compounds with the formulae I through VII, where $R_1$, $R_2$, $R_3$ and Z have the meanings indicated in the above.

Particularly suitable compounds according to the invention are those in which Z represents an optionally substituted alkylene groups containing 2-25 carbon atoms, an optionally substituted metha- or paraphenylene group, or an optionally substituted group having the formula

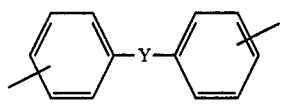    VIII where Y represents a —$CH_2$—, a —$C(CH_3)_2$—, a —O— or a —$SO_2$— group and $R_3$ an alkyl group with 1 to 6 carbon atoms.

The arrangement of the free bonds of the Z group as shown in formula VIII indicates that these bonds may be in ortho-, metha- or para-position relative to the Y-group.

Very suitable compounds according to the invention are (iso)maleimide-(iso)maleimide compounds with formulae I, II and/or III and (iso)maleimide-amide compounds with formulae IV and/or V where the Z group is chosen from

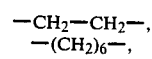
—CH₂—CH₂—,
—(CH₂)₆—,

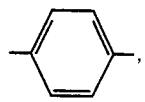

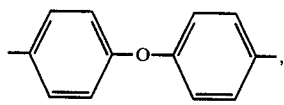

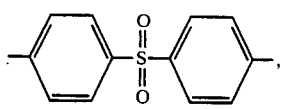

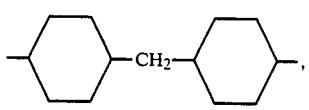

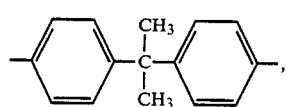

and

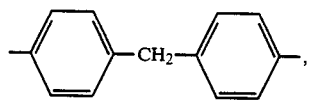

where $R_1$ and $R_2$ represent hydrogen and where $R_3$ represents an alkyl group with 1-6 carbon atoms.

By preference use is made of compositions containing as bismaleimide component one or more of the compounds with the formulae

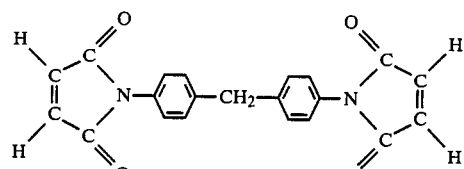

and/or

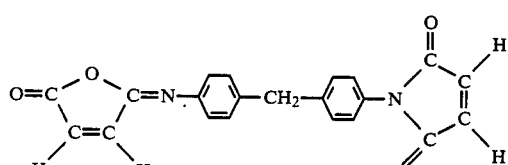

and/or

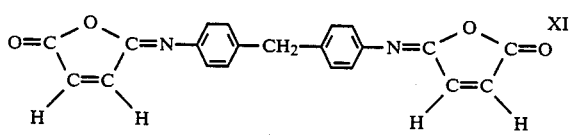

as maleimide-amide component one or more of the compounds with the formulae

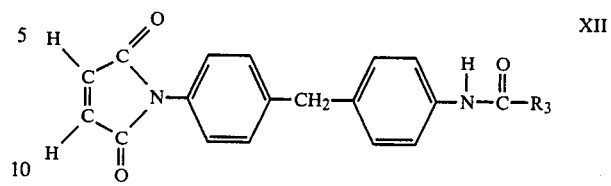

and/or

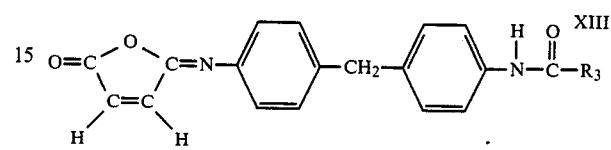

where $R_3$ represents an alkyl group with 1-6 carbon atoms, by preference methyl, and as maleic anhydride derivative maleic anhydride.

The compositions according to the invention that comprise 'bismaleimide compounds', 'maleimide-amide compounds' and an acid anhydride compound, contain from 80 to 30 wt. %, preferably from 75 to 45 wt. %, of the 'bismaleimide compounds', from 5 to 60 wt. %, preferably from 20 to 40 wt. %, of the 'maleimide-amide compounds' and from 1 to 10 wt. %, preferably from 2 to 7 wt. % of the malic anhydride derivative, preferably maleic anhydride.

The preparation of such compositions generally can be effected as indicated in the above. Preferably, but not necessarily, the reactions are effected in a suitable solvent, such as, acetone, methylethylketone, chloroform, ethyl acetate and toluene.

The ratio of 'bismaleimide compounds' to 'monomaleimide-amide compounds' to maleic anhydride derivative in the composition ultimately obtained can be controlled by the choice of the catalyst, and the amount of catalyst, by the setting of the reaction time and/or the reaction temperature, and by the setting of the amount of maleic anhydride derivative and/or alkylcarboxylic anhydride.

In particular, by preference a molar ratio of diamine to maleic anhydride derivative of between 1:1,75 and 1,2:1 is applied and an excess of the anhydride of the alkylcarboxylic acid relative to the maleic anhydride derivative used so as to achieve a 'bismaleimide':-'monomaleimideamide':maleic acid derivative ratio as preferred.

As alkylcarboxylic acid by preference acetic anhydride is applied.

In the reaction between the diamine and the maleic anhydride derivative by preference a temperature of 15° to 70° C. is applied, while the reaction time preferably varies between half an hour and 5 hours.

For the cyclodehydration reaction of the formed diamide acid by preference a temperature of 50° to 100° C. is applied, while the reaction time preferably varies between half an hour and 4 hours.

Catalysts that can be applied for the latter reaction are, for instance, sodium hydroxyde, sodium ethanolate, triethylamine, tri-(n-butyl)-amine, 2-vinyl pyridine, ion exchangers with hydroxyl groups, ethyl diamine tetraacetic acid (EDTA), N,N,N',N'-tetramethyl ethylene diamine (TMED) and 1,4-diazabicyclo-2,2,2-octane (DABCO). The best results, however, are obtained with TMED and DABCO.

As stated, the homogeneous, curable compositions according to the invention consist of an ethylenically unsaturated compound in combination with a 'bismaleimide'/'monomaleimide-amide'/maleic anhydride composition according to the invention in the indicated ratio and with optional further monomers and customary additives.

Ethylenically unsaturated compounds are here particularly understood to mean vinyl aromatic compounds such as: styrene, α-methylstyrene, para-methylstyrene, aminostyrene, hydroxystyrene, divinyl benzene, vinyl toluene; allyl compounds such as monoallyl esters or ethers and diallyl esters or ethers, for instance diallyl phthalate; vinyl ether and vinyl ester compounds such as vinyl benzoate; and acrylic acid esters and methacrylic acid esters.

Ethylenically unsaturated compounds can in broad ratios be mixed with the 'bismaleimide'/'monomaleimide-amide'/maleic anhydride compositions according to the invention, yielding homogeneous, curable compositions, in particular in ratios from 2:1 to 1:4. By preference ratios between 1:1.1 and 1:2.5 are applied.

Further also other (co)polymerizable compounds can be added insofar as these do not give rise to phase separation. In this respect, unsaturated polyesters, and prepolymers of diallyl esters and ethers, for instance prepolymers of diallyl phthalate, may also be considered.

In general such compounds are applied in an amount of at most 100 wt.-%, calculated relative to the other unsaturated components a and b and by preference in an amount of at most 50 wt.-%.

It further is to a limited extent possible to add customary substances such as inhibitors, pigments, fillers, reinforcing agents, shrinkage-controlling substances, etc. The term homogeneous relates only to the polymerizable part of the composition. Examples of possible additives are glass fibres, carbon fibres, metal fibres, aramid fibres, chalk, lime, sand, silica, aluminium oxide hydrate, polybutadiene, polystyrene, polyethylene, polypropylene and polyacrylates. For curing a radical source is added. As such, a hydroperoxide, a perester, a perketone and/or an other compound suitable for curing of styrene copolymers can be applied.

Curing takes place under the influence of radicals. The polymerization reaction can be effected both at a low temperature (less than 75° C.) and at elevated temperature.

The compositions according to the invention can be applied, for instance, as casting resin, laminating resin, etc.

The compositions according to the invention possess a combination of favourable properties. Before curing they are liquids, with a viscosity that generally is low at room temperature, that can well be applied for casting or impregnating. After curing at room temperature, preferably followed by after-curing at a higher temperature, for instance between 100° C. and 250° C., products are obtained that possess good mechanical and physical properties.

The invention will be elucidated on the basis of the following examples, without being restricted to the modes of realization described therein.

EXAMPLE 1

Preparation of a composition containing a 'bismaleimide', a 'maleimide-amide' and an acid anhydride compound At room temperature a solution of 100 g 4,4'-diaminodiphenyl methane in 300 ml acetone is trickled into 100 g maleic anhydride dissolved in 700 ml acetone. A precipitate of the corresponding dimaleimide acid is formed quantitatively. At 60° C. 150 g acetic anhydride and 1.5 g DABCO (1,4-diaza-bicyclo-(2,2,2)octane) is added; the anhydride serves as dehydrating agent and the amine as catalyst. The end of the reaction is characterized by the complete disappearance of the diamine acid precipitate. After removal of the solvent, acetic acid and acetic anhydride under a vacuum (0.1 mm Hg) and at 50°–100° C. a mixture is obtained, in quantitative yield, that consists of approx. 70% N,N',4,4'-diphenyl methane-bismaleimide, 25% 4-acetylaminophenyl-4'-maleimidophenyl-methane and approx. 5% maleic anhydride. In this mixture about 40% of 'maleimide' groups is present in the isomeric isomaleimide form and 60% in the maleimide form. This mixture is eminently suitable as basic ingredient for the preparation of thermosetting resins. This will be illustrated in the following examples.

EXAMPLES 2 AND 3

Preparation of a homogeneous, curable resin composition and curing of the same to obtain a copolymer object

EXAMPLE 2

An amount of 66 g of the composition according to Example 1 and 34 g styrene were introduced into a reaction vessel provided with a stirrer and placed in a bath that was kept at a temperature of 80°–100° C. by means of a thermostat. The mixture was stirred for 10–15 minutes, upon which it had changed into a clear, transparent, reddish solution. The solution, stabilized with 300 ppm benzoquinone, remained homogeneous even after cooling to 15°–20° C.

After degasification of the solution and addition of 1% methylethylketone peroxide (50% solution in dimethyl phthalate) the resin was cast into a rectangular metal mould (130×75×4 mm). In contrast to the usual procedure for unsaturated polyester resins, no accelerator was added. Curing took place at room temperature, the gelation time was about 20 minutes. After 8 hours, the sheet obtained was kept at a temperature of 80° C. for 24 hours, then at a temperature of 150° C. for 24 hours and at a temperature of 200° C. for another 24 hours. The properties of the objects obtained by casting are presented in Table A. The high HDT (heat distortion temperature) of the material is remarkable.

The hydrolytic stability of the product was also examined. To this end, test bars of the material with as dimensions 100×12.7×4 mm were submerged in deionized water in a pressure vessel. The test temperature was 120° C. As a criterion of the water resistance of the product, the flexural strength retention was used. This is understood to mean the percentage of the original flexural strength that remains when a test bar is subjected to the medium in question for a certain time. The results of these experiments are given in Table B. It is obvious that the resin composition to which the invention relates has a very good hydrolytic stability. Products on the basis of polyester and vinyl resins soon fail under these extreme conditions.

properties of cast objects on the basis of this resin are presented in Table A.

TABLE A

| Properties | Example 2 | Example 3 | Example 4 | Example 5 | Example 6 |
|---|---|---|---|---|---|
| E-modulus from bending test (ASTM D790), N/mm$^2$ | 3250 | 3050 | 7550 | 3070 | 3000 |
| Max. fibre stress (ASTM D790), N/mm$^2$ | 55 | 95 | 200 | 85 | 75 |
| Max. strain in the outer fibres from bending test (ASTM D790) in % | 1.9 | 3.2 | 3.4 | 2.8 | 2.5 |
| E-modulus from tensile test (ASTM D638-1), N/mm$^2$ | | 3950 | 9500 | 3900 | |
| Tensile strength (ASTM D638-1) N/mm$^2$ | | 30 | 105 | | |
| Elongation (ASTM D 638-1) in % | | 0.7 | 2.0 | | |
| HDT (ASTM 648) in °C. | 190 | 191 | | 172 | 165 |
| Barcol hardness (GYZJ 934-1) | 52 | 51 | 60 | 48 | 50 |

EXAMPLE 3

The instructions of Example 2 were repeated, this time however using a mixture consisting of 58 g of the composition according to Example 1, 29 g styrene and 13 g diallyl phthalate. The properties and hydrolytic stability of the cast objects as obtained under the conditions described in Example 2 are summarized in Table A and Table B respectively.

EXAMPLE 4

Preparation of a glass fibre reinforced product

The resin of the composition as given in Example 3 was used for the preparation of glass fibre reinforced products. A 4 mm thick laminate was built up of glass mats (Silenka, chopped strand mat, 450 g/m$^2$) and resin in such a way that the weight percentage of glass amounted to 33–35%. The mechanical properties of this laminate, which was cured according to the after-curing cycle described in Example 2, are presented in Table A.

EXAMPLE 5

Preparation and curing of a homogeneous, curable resin composition with addition of an amine compound To the resin as prepared via Example 3, 7 g benzyl amine was added at 80° C. Under these reaction conditions this amine adds rapidly to oleifinic imide unsaturations that are amply present in the mixture. The modified resin allows further processing and curing according to the method described in Example 2. The mechanical properties of the castings are included in Table A.

EXAMPLE 6

Preparation and curing of a homogeneous, curable resin composition with addition of a bis-citraconimide Mixing of 38 g of the composition according to Example 1, 20 g N,N'-4,4'-diphenyl methane-bis-citraconimide, 29 g styrene and 13% diallyl phthalate according to the instructions of Example 2 yields a dark red, clear, liquid composition. At 100° C. 7 g 4-hydroxy, 4-methyl pentanone-2 was added to this mixture and subsequently the resin was kept at 100° C. for about 20 minutes before being cooled to room temperature. The mechanical

TABLE B

| | Hydrolytic stability at 120° C. | | | |
|---|---|---|---|---|
| | flexural strength retention in % | | | |
| sample | t = 0 (blank) | 4 weeks | 8 weeks | 13 weeks |
| resin of Example 2 | 100 | 100 | 100 | 100 |
| resin of Example 3 | 100 | 100 | 100 | |

We claim:
1. A composition comprising:
(a) 80 to 30 weight percent of a bismaleimide having the formula

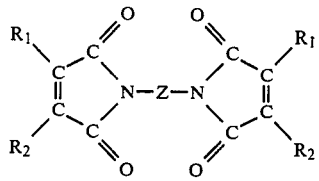

or an isomer thereof, wherein
$R_1$ and $R_2$ each independently represent hydrogen; an aliphatic, cycloaliphatic or aromatic group containing 1–12 carbon atoms; or halogen; or $R_1$ and $R_2$ together with the carbon atoms to which they are attached, form a ring system with at least one polymerizable C═C bond; and
Z represents a bivalent organic group,
(b) 5 to 60 weight percent of a maleimide-amide having the formula

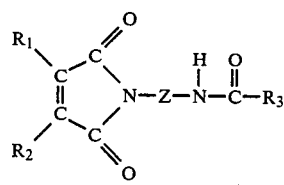

or an isomer thereof, wherein
$R_1$ and $R_2$ independently represent hydrogen; an aliphatic, cycloaliphatic or aromatic group containing 1–12 carbon atoms; or halogen; or $R_1$ and $R_2$ together with the carbon atoms to which they are attached, form a ring system with at least one polymerizable C=C bond, Z represents a bivalent organic group, and $R_3$ represents alkyl, substituted alkyl, cycloalkyl, aryl, aralkyl or alkylaryl, wherein the alkyl moieties have 1-12 carbon atoms, and (c) 1 to 10 weight percent of a maleic anhydride having the formula

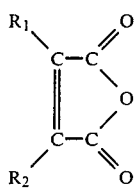

wherein $R_1$ and $R_2$ each independently represent hydrogen, an aliphatic, cycloaliphatic or aromatic group containing 1-12 carbon atoms; or halogen; or $R_1$ and $R_2$ together with the carbon atoms to which they are attached, form a ring system with at least one polymerizable C=C bond wherein said bivalent organic group Z is an optionally substituted alkylene group containing 2-25 carbon atoms, an optionally substituted metha or paraphenylene group, or

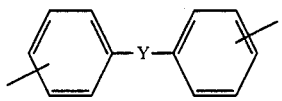

wherein Y is selected from the group consisting of —CH$_2$—, —C(CH$_3$)$_2$—, —O—, or —SO$_2$—.

2. The composition of claim 1 comprising (a) 80 to 30 weight percent of a bismaleimide having the formula

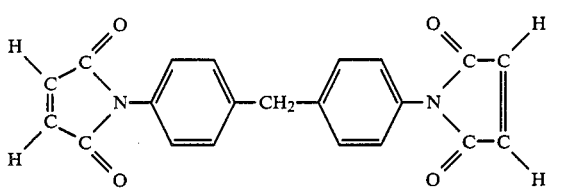

or an isomer thereof, (b) 5 to 60 weight percent of a maleimide-amide having the formula

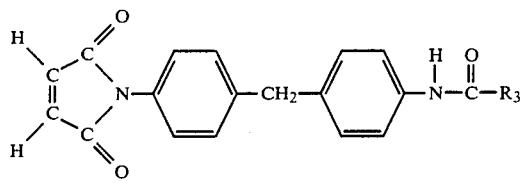

or an isomer thereof, wherein $R_3$ represents alkyl having 1-6 carbon atoms, and (c) 1 to 10 weight percent of maleic anhydride.

3. The composition of claim 2 wherein $R_3$ represents methyl.

4. The composition of claim 1 wherein said bismaleimide is present in an amount ranging from 75 to 45 weight percent, said maleimide-amide is present in an amount ranging from 20 to 40 weight percent, and said maleic anhydride is present in an amount ranging from 2 to 7 weight percent.

5. The composition of claim 1 wherein Z is a bivalent organic group independently selected from the group consisting of:

—CH$_2$—CH$_2$—,
—(CH$_2$)$_6$—,

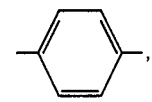

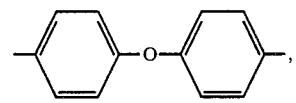

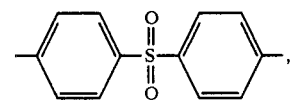

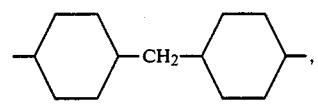

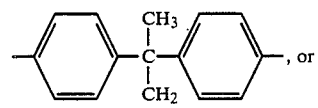, or

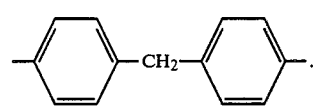

6. The composition of claim 1 wherein $R_3$ is an alkyl group having 1 to 6 carbon atoms.

7. The composition of claim 5, wherein $R_3$ is an alkyl group having 1 to 6 carbon atoms.

* * * * *